United States Patent [19]

Chazan, deceased et al.

[11] 4,130,640

[45] Dec. 19, 1978

[54] GERMICIDAL CLEANING COMPOSITIONS

[76] Inventors: Reuwen R Chazan, deceased, late of Savyon, Israel, by Dan Chazan, heir; David Y. Chazan, heir, both of Savyon, Israel; Eliezer Z. Fischer, 8 Levitan St., Ramat-Aviv, Tel-Aviv, Israel

[21] Appl. No.: 813,779

[22] Filed: Jul. 7, 1977

Related U.S. Application Data

[63] Continuation of Ser. No. 609,842, Sep. 2, 1975, abandoned.

[30] Foreign Application Priority Data

Sep. 10, 1974 [IL] Israel ........................................ 45639

[51] Int. Cl.$^2$ ................................................ A61K 31/79

[52] U.S. Cl. ........................................ 424/80; 424/150; 252/106

[58] Field of Search .................... 424/150, 80; 252/106

[56] References Cited

U.S. PATENT DOCUMENTS

| | | | |
|---|---|---|---|
| 2,776,924 | 1/1957 | Martin | 424/150 |
| 2,868,686 | 1/1959 | Shelanski et al. | 424/150 |
| 3,308,014 | 3/1967 | Cantor et al. | 424/150 |
| 3,687,855 | 8/1972 | Halpern | 424/150 |

*Primary Examiner*—V. D. Turner

*Attorney, Agent, or Firm*—Ladas, Parry, Von Gehr, Goldsmith & Deschamps

[57] ABSTRACT

A germicidal cleansing composition of matter, in semi-solid form, comprising in combination:

a. at least 20 weight-% of one or two members of the group consisting of sulfated fatty alcohols ($C_{14}$ to $C_{26}$) and of sulfosuccinates of fatty alcohols ($C_{12}$ to $C_{24}$);

b. between 1 weight-% and 20 weight-% of an organic iodine complex or of solubilized inorganic iodine;

c. a quantity of not exceeding about 10 weight-% of water;

d. at least about 20-weight-% of one or more members of the group consisting of saturated fatty alcohols ($C_{14}$ to $C_{26}$), saturated fatty acids ($C_{14}$ to $C_{20}$) and succinates or maleates of fatty alcohols ($C_{10}$ to $C_{24}$). Preferred iodine compounds are iodophors, such as PVP-iodine, undecoylum-chloride iodine, imidazoline iodine; or inorganic iodine compounds such as iodine and an alkali metal iodide.

7 Claims, No Drawings

GERMICIDAL CLEANING COMPOSITIONS

This is a continuation of application Ser. No. 609,842 filed Sept. 2, 1975, now abandoned.

SUMMARY OF THE INVENTION

The present invention relates to novel germicidal cleansening compositions of matter, in semi-solid form, the germicidal action of which is based on the combined effect of iodophors or on inorganic iodine and iodine compounds, in combination with constituents giving a detergent effect. The novel compositions of matter are of special use for disinfecting various items in hospitals and the like, for use before surgery and the like. The novel products according to the present invention are substantially non-hygroscopic, non-corrosive and they have a long-lasting germicidal or germistatic effect and they are enhanced by outstanding detergent properties. The term "semi-solid form" defines a form like that of soap bars or of solid detergent sticks or the like.

The novel compositions according to the present invention comprise essentially in combination:

(a) at least 20 weight-% of one or two of the group consisting of sulfated fatty alcohols ($C_{14}$ to $C_{26}$) and of sulfosuccinates of fatty alcohols ($C_{12}$ to $C_{24}$);

(b) between 1 weight-% and 20 weight-% of an organic iodine complex or of solubilized inorganic iodine;

(c) a quantity of not exceeding about 10 weight-% of water;

(d) at least about 20 weight-% of one or more members of the group consisting of saturated fatty alcohols ($C_{14}$ to $C_{26}$), saturated fatty acids ($C_{14}$ to $C_{20}$) and succinates or maleates of fatty alcohols ($C_{10}$ to $C_{24}$). Preferred iodine compounds are iodophors, such as PVP-iodine, undecoylum-chloride iodine, imidazoline iodine; or inorganic iodine compounds such as iodine and an alkali metal iodide.

Other and further more detailed aspects of the invention will become apparent hereinafter.

STATE OF THE PRIOR ART

There are known various germicidal preparations based on iodophors, such as, for example, those described in U.S. Pat. No. 3,687,855, and in German Pats. 2,123,551 and 2,166,215. These contain considerable quantities of extenders, such as polyethylene glycol and other polyhydroxy compounds. The inclusion of these was considered imperative according to these patents.

According to the present invention there is provided a novel composition of matter devoid of such extenders. The novel composition of matter comprises a sulfosuccinate and/or succinate of fatty alcohols and this obviates the necessity for the inclusion of bulky extenders which are inert and non-active. The presence of the sulfosuccinates and/or succinates enhances the detergent properties of the novel composition of matter and increases the germicidal properties of same due to the synergistic properties of this mixture.

THE PRESENT INVENTION

As set out above, the novel germicidal cleansening compositions in semi-solid form according to the present invention comprise at least 20 weight-% and up to about 70 weight-% of one or two members of the group consisting of sulfated fatty alcohols and sulfosuccinates of fatty alcohols; between about 1 weight-% and 20 weight-% of an organic iodine complex or of solubilized inorganic iodine; a quantity of up to about 10 weight-% of water; at least about 20 weight-% of one or more of: saturated fatty alcohols, saturated fatty acids and succinates or maleates of fatty alcohols. In these, the carbon-atom range is as defined above. The saturated fatty alcohols are preferably of the R—OH type, where R designates alkyl of about 14 to 26 carbon atoms. The sulfated fatty alcohols are of the R'—O—$SO_2$—ONa type, where R' designates alkyl of 10 to about 26 carbon atoms. The fatty acids are of the type R"-COOH where R" is alkyl of about 14 to 20 carbon atoms. The sulfosuccinates are mono- and/or di-sulfo-succinates of fatty alcohols of the respective formulas

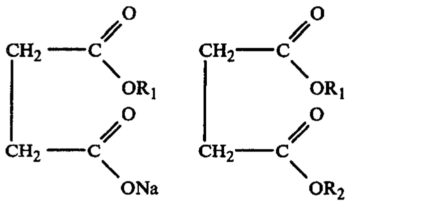

and

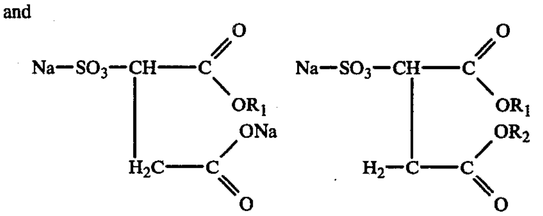

wherein $R_1$ and $R_2$, which may be identical or different, each represents an alkyl group or an alkoxylated alkyl group.

Suitable active iodine compounds are those generally known as "iodophors" i.e. products wherein a surface active agent serves as carrier and solubilizing agent for iodine, compounds such as PVP-I iodine-polyvinylpyrrolidone complex; undecoylum-chloride iodine, imidazoline iodine and the like or inorganic iodine such as iodine in combination with an alkali metal iodide such as potassium iodide or sodium iodide. These constitute about 1 to 20 percent by weight of the compositions of the invention, the preferred range being about 2 to 10 weight-%. Various of the different active iodine complexes and compounds were tested and satisfactory results were obtained. It is evident that the combination of such active iodine complexes or compounds with the other constituents of the novel compositions result in a synergistic germicidal effect.

The iodine content of the compositions can be varied according to the desired use and degree of germicidal activity. It is known that concentrations as low as about 10 ppm of iodophor in aqueous systems exhibit a pronounced batceriostatic effect.

The other components sulfated fatty alcohols and sulfosuccinates (as defined above) of fatty alcohols are substantially interchangeable, and these impart the main detergent properties to the novel compositions. The novel compositions contain generally not less than about 20 weight-% of these two or of one of these.

The saturated fatty alcohols, saturated fatty acids and also the succinate of fatty alcohols impart advantageous dermatological characteristics to the compositions of the invention. These two are interchangeable to a large extent. The choice of the relative quantities depends to a large extent on the desired quantity of lather desired.

A part or all of the succinate used in the compositions of the present invention may be replaced by corresponding quantities of maleates.

Satisfactory results can be achieved with various combinations of the 3 ingredients: saturated fatty alcohols, saturated fatty acids and succinates (or partially maleates) of fatty alcohols, which comprise about up to 70 to 80 parts by weight of the compositions of the present invention. These (or any of these) three ingredients ought to constitute at least about 20 parts by weight of the compositions of the invention. When such low quantities of these are used, the other components such as sulfated fatty alcohols and/or sulfosuccinates of fatty alcohols will constitute a correspondingly higher percentage of the composition. Such compositions have a high lathering activity.

The sulfosuccinates have a pH in the desired acid range, and the succinate has also a pH in the desired acid range. These serve also as buffering agents in this range.

The novel germicidal semi-solid preparations are advantageously prepared by heating the various ingredients together at an elevated temperature, to obtain an intimate fluid or semi-fluid mixture, cooling the mixture to a lower temperature at which it is still in a semi-fluid extrudable state, adding thereto the iodine-complex, or inorganic iodine, and extruding, casting or shaping by other means the product in a desired shape, such as bar, stick or the like.

Some of the preparations were initially heated to about 70°-85° C., cooled to about 50°-65° C., the iodine complex or inorganic iodine was added and the desired shape of the final product was prepared.

The pH of the preparation is advantageously adjusted to a pH in the acid range, which ought to be in the range suited for dermal applications. The best pH is about pH 5, and this can be attained by the addition of suitable physiologically acceptable acids. Various organic acids are suited for this purpose; so is phosphoric acid. The fatty acids are advantageously part of the compositions of the present invention, but these do not form an imperative part thereof.

PREFERRED EMBODIMENTS

EXAMPLE 1

70 parts by weight lauryl alcohol sulfate (90% active ingredient, 10% water) was heated to 80° C. and mixed with 20 parts acetyl/steary alcohol and 5 parts stearic acid. The pH was adjusted by the addition of lactic acid (about 1% by weight) to pH 5.0 and 4 parts P.V.P.-Iodine was added at a temperature of 55° C. The product was cast in the form of soap-bars.

EXAMPLE 2

A preparation was prepared from 45 percent by weight fatty alcohol sulfates (60% lauryl, 30% myristyl and 10% cetyl alcohol) and this was mixed with 20% myristyl sulfosuccinate. After heating to 80° C. the mixture was admixed with 24% of its weight of technical grade cetyl/stearyl alcohol. The pH was adjusted by addition of phosphoric acid to pH 5, cooled to 60° C. and 10% by weight of polyvinyl pyrrolidone iodine was added. The mixture was extruded in the form of soap bars.

The following preparations, given in the form of a Table illustrate the composition of a number of variations according to the present invention. It ought to be clearly understood that the percentages of the ingredients are not critical, and that these may be varied within certain limits without departing from the scope and spirit of the present invention. The various percentages are to be adjusted mutually, and these depend also to a certain extent on the desired degree of hardness of the product.

The following preparations were made as set out above, parts are by weight:

| | I | II | III | IV | V | VI | VII | VIII |
|---|---|---|---|---|---|---|---|---|
| Sulfated fatty alcohols ($C_{10}-C_{26}$): | 20 | 30 | 35 | 40 | 30 | 30 | 5 | 20 |
| Saturated fatty alcohols ($C_{14}-C_{26}$): | 25 | 18 | 15 | 5 | 7 | 20 | 15 | 35 |
| Saturated fatty acids ($C_{14}-C_{20}$): | 8 | — | 5 | 10 | — | 10 | 46 | 15 |
| Sulfosuccinate of fatty alcohols ($C_{12}-C_{24}$): | 35 | 36 | 18 | 18 | 40 | 0 | 17 | 10 |
| Succinate of fatty alcohols ($C_{10}-C_{24}$): | 5 | | 9 | 14 | — | 24 | 10 | 10 |
| Iodophor(PVP-I or non-ionic detergent-I complex): | 7 | 10 | 10 | 5 | 15 | 10 | 2 | 0 |
| Iodine and KI: | 0 | 0 | 0 | 0 | 0 | 0 | 0 | 5 |
| Water: | — | 5 | 8 | 8 | 8 | 6 | 5 | 5 |

Instead of the organic iodine complexes there may be used inorganic iodine preparations, such as for example, compositions containing iodine and an alkali metal iodide, such as potassium iodide, dissolved in a suitable quantity of water. For example, 20 wt-% iodine, 40 wt-% potassium iodide and 40 wt-% water give a suitable solution. A quantity of 4 g. of this solution incorporated in 96 g of detergent mixture according to the invention (with no organic iodine complex) gave satisfactory detergent and antiseptic results.

Similar compositions were prepared, containing a quantity of an organic acid such as citric or lactic acid, adapted to adjust the pH to a value of about 5-5.5.

Stability

The stability of the novel germicidal preparations according to the present invention was tested.

The tests carried out have shown that, for example, a preparation according to the present invention containing 10 percent by weight Povidone Iodine (pH 5.3) lost only 6 percent of the available iodine during a period of storage of 50 days at 50° C. A liquid detergent preparation, available commercially, containing the same initial percentage of iodine lost 27 percent available iodine at 50° C. during 30 days. Comparative tests have shown the superiority of preparations according to the present invention as regards storage, compared with other commercial preparations containing Povidone Iodine.

The pH of the preparations according to the present invention is an optimum as regards the activity of the iodine. It is known that the bactericidal efficacy of iodine and of organic iodine preparations is increased when the pH is lowered. A pH of below 6 is generally suggested, the activity being still better at a pH of about 5 or below this value.

The preparation according to the present invention has a pH in the optimal range, while the advantageous detergent properties of a good soap are maintained. The preparations according to the present invention are not detrimentally effected by hard water. No "ring" is formed in the bathtub and no precipitates are formed with hard water or with salts such as magnesium or calcium salts.

The pH of the preparation according to the present invention can be adjusted to the desired value by the addition of various physiologically acceptable acids such as lactic acid, citric acid, phosphoric acid, fumaric acid, tartaric acid and the like.

The novel preparations according to the present invention have a further advantage, namely the enhanced effect of the detergent and of the organic iodine compounds. In soaps containing organic iodine compounds, hard water causes the formation of a precipitate and this impairs the antibacterial effectivity. The novel compositions are not adversely affected by hard water, and the detergent effect and the bacteriacidal effect of the organic iodine compound complement each other and a certain synergism is obtained.

Conventional soaps used in places like hospitals are often the source of cross-infections due to the fact that bacteria may survive on the surface of such solid soap bars and infect subsequent users.

The bactericidal effect of the novel preparations is so strong that practically no patogenic microorganism will survive on the surface of a preparation according to the invention. This property is of special importance for use in hospitals, in the case of epidemics, in military medicine, nurseries and other public places.

Bacteriological Tests

A bar was prepared according to Example 4, and a suspension of $6.10^8$ stphylococci was applied onto the surface of the bar, which had been wetted with tap water 3 minutes before. Sixty seconds after the application of the bacteria, a swab was taken and cultured. No bacteria survived.

A control was carried out with conventional toilet soap, and over 1000 bacteria were counted.

A suspension of about $10^5$ pseudomonas aeruginosa was applied to the palm of a human hand and spread thereon. The hand was washed with soap during two minutes of scrubbing and rinsed with water. About 680 microorganisms were counted.

A parallel test with a bar of the novel preparation according to Example 4 resulted in zero survival of microorganisms.

A slurry was prepared comprising 10 g. of a composition according to preparation No. III in 20 ml. of water. A quantity of Pseudomonas Aeroginosa was introduced into the slurry so as to obtain a final concentration of $10^5$ microorganisms per ml.

After 30 minutes, a sample was taken and examined. No bacteria survived alive.

A similar experiment was carried out with regular soap at similar concentrations in water and of bacteria. After 30 minutes the bacteria survived. Even after 2 hours they were still alive.

Similar results were obtained with analogous preparations containing inorganic iodine in combination with sodium iodide or potassium iodide.

We claim:

1. A germicidal composition in, bar-soap form comprising in combination:
   a. 20 weight-% to 70 weight-% of a member selected from the group consisting of sulfated fatty alcohols ($C_{14}$ to $C_{26}$), sulfosuccinates of fatty alcohols ($C_{12}$ to $C_{24}$) and mixtures thereof;
   b. between 1 and 20 weight-% of an iodophor selected from the group consisting of an organic iodine complex, and iodine in combination with potassium or sodium iodide;
   c. a quantity not exceeding about 10 weight-% of water;
   d. 20 weight-% to 60 weight-% of a member selected from the group consisting of saturated fatty alcohols ($C_{14}$ to $C_{26}$), saturated fatty acids ($C_{14}$ to $C_{20}$), succinates or maleates of fatty alcohols ($C_{10}$ to $C_{24}$) and mixtures thereof.

2. A germicidal composition according to claim 1, wherein component (a) comprises between 25 and 50 weight-% of the composition.

3. A germicidal composition according to claim 1, containing an organic acid adapted to adjust the pH to about pH 5.

4. A germicidal composition according to claim 1, wherein component (b) is polyvinylpyrrolidone-iodine complex.

5. A germicidal composition according to claim 1, wherein component (b) is iodine in combination with potassium iodide or sodium iodide.

6. A composition according to claim 4, wherein said polyvinylpyrrolidone-iodine complex comprises from 2 to 10 weight-%.

7. A germicidal composition according to claim 1, wherein the saturated fatty alcohols, saturated fatty acids and succinates of fatty alcohols comprise from 30 to 60 weight-% of the composition.

* * * * *